United States Patent [19]
Mori et al.

[11] 4,117,247
[45] Sep. 26, 1978

[54] PREPARATION OF 1,1,1-TRIHALOGENO-4-METHYL-3-PENTEN-2-OL

[75] Inventors: Fumio Mori, Kurashiki City; Yoshiaki Omura, Okayama; Takashi Nishida; Kazuo Itoi, both of Kurashiki, all of Japan

[73] Assignee: Kuraray Co., Ltd., Kurashiki, Japan

[21] Appl. No.: 786,587

[22] Filed: Apr. 11, 1977

Related U.S. Application Data

[63] Continuation-in-part of Ser. No. 616,999, Sep. 26, 1975, abandoned.

[30] Foreign Application Priority Data

Oct. 3, 1974 [JP] Japan .............................. 49-114114
Oct. 3, 1974 [JP] Japan .............................. 49-114115
Dec. 28, 1974 [JP] Japan .............................. 49-2064
Dec. 28, 1974 [JP] Japan .............................. 49-2065
Jun. 30, 1975 [JP] Japan .............................. 50-80600

[51] Int. Cl.$^2$ .............................................. C07C 33/10
[52] U.S. Cl. ..................................... 568/845; 71/122
[58] Field of Search ...................................... 260/633

[56] References Cited
FOREIGN PATENT DOCUMENTS 7,511,584  4/1976  Netherlands ............................ 260/633
227,012    1/1969  U.S.S.R. ................................. 260/633

OTHER PUBLICATIONS

Mackenzie, Chemistry of Alkenes, vol. 2, Interscience Publishers, New York (1970), edited by Zabicky, pp. 164–167.
Ipatieff et al., J.A.C.S., 56 2696–2698 (1934).
March, Advanced Org. Chem., Reaction Mechanism & Structure, McGraw–Hill Book Co., New York (1968), pp. 452–454.
Klimova et al., J. Org. Chem., USSR (1969), pp. 1308–1311.
Colonge et al., Soc. Chem. de France Bull (1957), 204–208.
Colonge et al., C.R. 1954, 541–543.
Bishop et al., J. Chem. Soc., 1966, 670–673.
Yanovskaya et al., Russian Chemical Reviews, 39 (10) 1970, pp. 859–870.

Primary Examiner—Howard T. Mars
Attorney, Agent, or Firm—Bacon & Thomas

[57] ABSTRACT

A 1,1,1-trihalogeno-4-methyl-3-penten-2-ol is prepared by thermally isomerizing 1,1,1-trihalogeno-4-methyl-4-penten-2-ol. The isomerization reaction may be catalyzed by an acid or a transition metal of Group 6B, 7B or 8 of the Periodic Table of Elements, or a compound thereof. The 1,1,1-trihalogeno-4-methyl-3-penten-2-ol thus prepared is useful as a synergist for herbicides or a physiologically active compound, and, additionally, is useful as a starting material for the synthesis of 2,2-dimethyl-3-(2′,2′-dihalogenovinyl)-cyclopropane carboxylic esters which are active ingredients of insecticides.

4 Claims, No Drawings

PREPARATION OF 1,1,1-TRIHALOGENO-4-METHYL-3-PENTEN-2-OL

CROSS REFERENCE TO RELATED APPLICATION

This application is a continuation-in-part of our earlier copending application, Ser. No. 616,999, filed Sept. 26, 1975 and now abandoned.

BACKGROUND OF THE INVENTION

1. Field of the Invention

The present invention relates to a process for preparing a 1,1,1,-trihalogeno-4-methyl-3-penten-2-ol of the formula [I]:

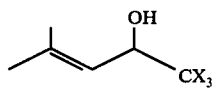

wherein each X represents Cl or Br, comprising thermally isomerizing a 1,1,1-trihalogeno-4-methyl-4-penten-2-ol of the formula [II]:

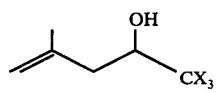

wherein each X is as defined above.

The topic thermal isomerization, conducted at a temperature in the range of from about 100° to about 250° C., is advantageously, albeit not necessarily, carried out and/or promoted in the presence of an acid catalyst, a transition metal catalyst, or a transition metal compound catalyst. In the event the thermal isomerization is acid catalyzed, the reaction can be conducted at a temperature in the range of between 50° and 250° C.

2. Description of the Prior Art

The 1,1,1-trihalogeno-4-methyl-3-penten-2-ol [I] obtained by the process of the present invention can be utilized for a variety of purposes. For example, 1,1,1-trichloro-4-methyl-3-penten-2-ol is a useful synergistic agent for herbicides [see U.S.S.R. Pat. No. 227,012] and is also known to be physiologically active. In addition, the 1,1,1-trihalogeno-4-methyl-3-penten-2-ol [I] has utility as a starting material in the synthesis of acid components of 2,2-dimethyl-3-(2',2'-dihalogenovinyl) cyclopropane carboxylic esters which exhibit remarkable insecticidal action [see published Japanese Patent Application, Ser. No. 47531/1974, corresponding to British Patent Specification No. 1,413,491, and D. G. Brown et al., *J. Agr. Food Chem.*, 21, No. 5,767 (1973)]. 2,2-Dimethyl-3-(2',2'-dihalogenovinyl) cyclopropane carboxylic esters can be synthesized by reacting the 1,1,1-trihalogeno-4-methyl-3-penten-2-ols with orthoacetic esters or ketene acetals with or without the aid of an acid catalyst to obtain 3,3-dimethyl-4,6,6-trihalogeno-5-hexenoic esters and then treating such esters with a basic reagent. According to this process, cyclopropane carboxylic acid esters can be prepared more easily and at a lower cost as compared to those produced by known processes.

1,1,1-Trichloro-4-methyl-3-penten-2-ol is a known compound and can be synthesized by Grignard reaction as follows [*J. Chem. Soc.*, (C), 670 (1966)]:

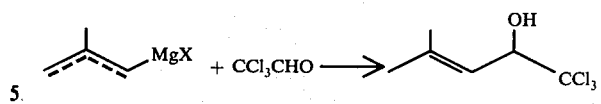

wherein X represents Cl or Br, and

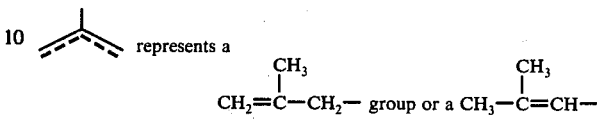

group. However, this conventional process has drawbacks in that the Grignard compounds used as starting materials cannot be prepared easily and are needed in stoichiometric amounts which are substantial and hence no economical.

Although Colonge et al report [*Soc., chem de France, Bull*, 204-208 (1957)][1], that isobutene reacts with chloral in the presence of aluminum chloride at −5°−+10°, forming a mixture of 30% 1,1,1-trichloro-4-methyl-4-penten-2-ol and 70% 1,1,1-trichloro-4-methyl-3-penten-2-ol, it has been subsequently proven by Klimova et al[2] that Colonge et al erroneously identified the structure of the adduct they obtained and that isobutene reacts with chloral in the presence of aluminum chloride at 0° to selectively form 1,1,1-trichloro-4-methyl-4-penten-2-ol. If 1,1,1-trichloro-4-methyl-4-penten-2-ol could be easily converted into 1,1,1-trichloro-4-methyl-3-penten-2-ol, the process would be economically superior to the aforementioned Grignard process in preparing said 1,1,1-trichloro-4-methyl-3-penten-2-ol.

[1] Cf. Colonge et al, *C.R.*, 541-543 (1954)
[2] Klimova et al, *J. Org. Chem., U.S.S.R.*, 1308-1311 (1969)

Although there are many reports concerning the migration of double bonds in olefins, it is true, as Yanovskaya et al reported [*Russian Chemical Review*, 39 (10) (1970)] that the migration of double bonds in olefins is not directly dependent upon the type of the olefin, the situation of any substituent on the olefin and the nature of any solvent employed. For example, in the case of unsubstituted nitro-olefins or derivatives substituted only in the α-position, the β,γ-isomer is wholly displaced towards the α,β-isomer,

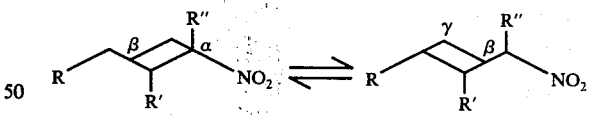

whereas in the case of nitro-olefins substituted in the β- or γ-positions, the β,γ-isomer is not completely displaced towards the α,β-isomer so as to obtain an equilibrium mixture of major amounts of α,β-isomer and appreciable amounts of the β,γ-isomer. Moreover, unsubstituted vinylnitriles or derivatives with substituents only in the α- or β-positions do not isomerize to β,γ-isomer from α,β-isomer.

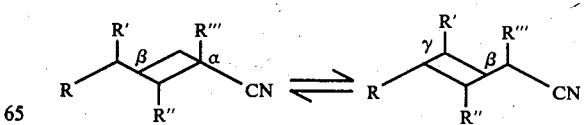

When encountering two methyl groups or electron-accepting substituents ($C_6H_5$, $C_6H_5O$) in the γ-positions, the α,β-isomer is displaced towards the β,γ-isomer. However, the γ-substituted vinylnitrile does not isomerize where there is a methyl group in the α-position.

Furthermore, 3-methyl-3-buten-1-ol, which has a molecular structure very similar to 1,1,1-trihalogeno-4-methyl-4-penten-2-ol, is only slight isomerized to 3-methyl-2-buten-1-ol under heat in both an uncatalyzed reaction and one employing p-toluenesulfonic acid [compare Reference Examples 14 and 15 described hereinafter].

Thus, there exists a need in the art for a simple and inexpensive method of isomerizing 1,1,1-trihalogeno-4-methyl-4-penten-2-ol to 1,1,1-trihalogeno-4-methyl-3-penten-2-ol with high selectivity for the latter.

SUMMARY OF THE INVENTION

Accordingly, it is a primary object of the present invention to provide an improved means of preparing 1,1,1-trihalogeno-4-methyl-3-penten-2-ol from 1,1,1-trihalogeno-4-methyl-4-penten-2-ol, such preparation being optionally promoted and/or carried out in the presence of an acid catalyst, a transition metal catalyst, or a transition metal compound catalyst.

According to the process of the present invention, 1,1,1-trihalogeno-4-methyl-3-penten-2-ol[I] can be prepared in a far easier and less expensive manner than has been previously known for the following reasons:

(i) The isomerization reaction can be effected easily and efficiently; and (ii) The 1,1,1-trihalogeno-4-methyl-4-penten-2-ol[II] starting material can be prepared easily by reacting isobutene with trihalogenoacetaldehydes, such as chloral and bromal, in the presence of a Lewis acid catalyst, such as aluminum chloride or tin tetrachloride [see *Chem. Abst.*, 71, 112335 k].

DETAILED DESCRIPTION OF THE INVENTION

According to one embodiment of the invention a temperature range of 100°–250° C. is employed in heating 1,1,1-trihalogeno-4-methyl-4-penten-2-ol[II] in the absence of catalyst to achieve the isomerization by shifting the position of the double bond. At temperatures below 100° C. the rate of the isomerization is low. At a temperature above 250° C., selectivity to 1,1,1-trihalogeno-4-methyl-3-penten-2-ol[I] is decreased. The temperature of isomerization is preferably 140° to 200° C.

The isomerization reaction proceeds as heating time elapses. Finally, the 1,1,1-trihalogeno-4-methyl-4-penten-2-ol[II] and the 1,1,1-trihalogeno-4-methyl-3-penten-2-ol[I] form an equilibrium composition of about 15:85 which remains unchanged, unless the 1,1,1-trihalogeno-4-methyl-3-penten-2-ol[I] is removed from the reaction system.

The isomerization reaction can be performed batchwise or continuously. In order to achieve high selectivity, it is considered desirable to use a highly pure 1,1,1-trihalogeno-4-methyl-4-penten-2-ol[II] starting material, and to effect the reaction under an inert gas atmosphere such as nitrogen or argon.

While solvents are not always required in the isomerization reaction, those which do not interfere with the reaction, such as n-hexane, n-octane, benzene, toluene, p-xylene, di-n-butylether, carbon tetrachloride, chloroform, ethyl acetate, ethanol and acetic acid, can advantageously be used.

According to another embodiment of the invention, the reaction mass is heated in the presence of an acid, or at least one substance comprising a member selected from the group consisting of transition metals of Groups 6B, 7B and 8 of the Periodic Table of Elements and compounds of said transition metals to improve the rate of the isomerization of the double bond and thereby decrease the time required for attaining the equilibrium composition or a desired conversion.

The acid catalysts used in the present invention are selected from the group consisting of sulfonic acids such as o-, m- or p-toluenesulfonic acid, benzenesulfonic acid, naphthalenesulfonic acid, laurylsulfonic acid, 4-chloro-2-methylbutane-2-sulfonic acid; ion exchange resins containing sulfonic acid groups or carboxyl groups as the ion exchange group; and inorganic acids such as sulfuric acid, phosphoric acid and hydrochloric acid. Of the above, benzenesulfonic acid, o-, m- or p-toluenesulfonic acid, Amberlyst H [trade name of an ion exchange resin of Organo Co., Ltd.], sulfuric acid and phosphoric acid are preferred.

The amount of the acid catalyst required depends upon the particular acid used, but it is usually within the range of about 0.1–30 wt. % based on the weight of the reactant 1,1,1-trihalogeno-4-methyl-4-penten-2-ol[II]. If the amount is below about 0.1 wt.%, the effect of the catalyst is insignificant. On the other hand, amounts above 30 wt.% do not significantly increase the rate, and therefore, are uneconomical. The preferred amount of the acid catalyst is in the range of about 0.1–5 wt.%.

When an acid catalyst is used, the isomerization reaction is effected by heating the reaction system to a temperature in the range of 50°–250° C., preferably 60°–170° C.

The other catalysts having utility in the process of the invention comprise members selected from the group consisting of transition metals of Groups 6B, 7B and 8 of the Periodic Table of Elements, such as Cr, Mn, Co, Ni, Ru, Rh, Pt, Pd, W or Ir, and compounds of said transition metals as, for example, the metal oxides, inorganic acid salts, organic acid salts and metal complexes. Exemplary of these compounds are chromium (III) acetylacetonate, molybdenum disulfide, tungsten trioxide, manganese (III) acetylacetonate, ruthenium trichloride, cobalt (II) acetylacetone, cobalt hexamine chloride, rhodium (III) acetylacetonate, rhodium trichloride, iridium trichloride, Raney nickel, Raney cobalt, nickel (II) acetylacetonate, palladium chloride, palladium black, palladium oxide and 5% palladium/carbon.

Generally, the transition metal or transition metal compound catalysts are used in amounts in the range of 0.001–30 wt.%, preferably 0.1–10 wt.%, based on the weight of the 1,1,1-trihalogeno-4-methyl-4-penten-2-ol[II]. The catalyst can also be borne by a suitable carrier or support.

When such a transition metal or compound thereof is used as the catalyst, the isomerization reaction is effected by heating the reaction system to a temperature in the range of 100°–250° C., preferably 140°–200° C.

Of the 1,1,1-trihalogeno-4-methyl-3-penten-2-ols[I] obtained by the process of the instant invention, 1,1,1-trichloro-4-methyl-3-penten-2-ol is known in the art, but 1,1,1-tribromo-4-methyl-3-penten-2-ol is a new compound.

The 1,1,1-trihalogeno-4-methyl-3-penten-2-ol[I], prepared in accordance with the invention, have utility as the starting material in the synthesis of the acid component of 2,2-dimethyl-3-(2',2'-dihalogenovinyl) cyclopropane carboxylic esters which are useful intermediates for the synthesis of certain valuable insecticides. Another use of the reaction mixture obtained by the isomerization reaction of the present invention is as the starting material in the preparation of 3,3-dimethyl-4,6,6-trihalogeno-5-hexenoic ester by reaction with orthocarboxylic ester or ketene acetal with heating. The 1,1,1-trihalogeno-4-methyl-3-penten-2-ol[I] contained in said reaction mixture is used in either the isolated and purified form or without isolation and purification. When the isomerization reaction is conducted in the presence of an acid catalyst, especially sulfonic acid, the reaction mixture may be used without isolating the 1,1,1-halogeno-4-methyl-3-penten-2-ol[I] for preparing 3,3-dimethyl-4,6,6-trihalogeno-5-hexenoic ester in high yield. Thereafter, 3,3-dimethyl-4,6,6-trihalogeno-5-hexenoic ester may be converted to 2,2-dimethyl-3-(2',2'-dihalogenovinyl)-cyclopropane carboxylic ester in high yield by treatment with a basic reagent.

The 1,1,1-trihalogeno-4-methyl-4-penten-2-ol[II] employed by the process of the present invention can be synthesized in numerous ways including reacting 1,1,1-trihalogenoacetaldehydes, such as 1,1,1-trichloroacetaldehyde [hereinafter referred to as chloral] or 1,1,1-tribromoacetaldehyde [hereinafter referred to as bromal], with isobutene.

The reaction of trihalogenoacetaldehyde with isobutene can be promoted by adding an acid catalyst to the reaction system. Exemplary of the acid catalysts are:

(i) Lewis acids such as aluminum chloride, aluminum bromide, boron trifluoride-diethyl ether, zinc chloride, ferric chloride, tin tetrachloride, tin dichloride, tin tetrabromide, titanium tetrachloride, thallium trichloride, bismuth trichloride, tellurium tetrachloride, tellurium dichloride, antimony pentachloride and phosphorus pentoxide;

(ii) inorganic acids such as sulfuric acid, phosphoric acid and hydrochloric acid; and (iii) organic acids such as sulfonic acids, as for example, benzenesulfonic acid, o-, m- and p-toluenesulfonic acids.

The preferred acid catalysts are aluminum chloride, aluminum bromide, zinc chloride, tin tetrachloride, boron trifluoride-diethyl ether, sulfuric acid and phosphoric acid.

The amount of the acid catalyst required depends upon the particular acid chosen, but generally is in the range of about 0.5–30 molar%, preferably 3–15 molar% based on the amount of trihalogenoacetaldehyde charged.

The amount of isobutene charged is selected from a range of about 0.5–6 moles per mole of trihalogenoacetaldehyde. However, to achieve the most efficient utilization of the trihalogenoacetaldehyde charged, it is preferred to use 1.0–4 moles of isobutene per mole of trihalogenoacetaldehyde.

While the reaction may be performed at low temperatures, for example, −20° to 0° C., to maintain the isobutene in liquid form by adding the catalyst slowly under atmospheric pressure, the reaction can also be carried out at higher temperatures, under elevated pressure, if desired.

Reaction solvents are not necessary, but any solvent which does not participate in the reaction, such as petroleum ether, n-pentane, n-hexane, and nitromethane, may be used.

The 1,1,1-tribromo-4-methyl-4-penten-2-ol prepared by the aforenoted process is a new compound.

In order to further illustrate the present invention and the advantages thereof, the following specific examples are given, it being understood that their sole purpose is illustrative and in no way are intended to limit the scope of the invention.

In the following examples, all parts are given by weight.

EXAMPLE 1

33 Parts of 1,1,1-trichloro-4-methyl-4-penten-2-ol [purity: above 98%] were stirred at 140°–150° C. for a predetermined time period under an atmosphere of nitrogen. The contents of the reaction vessel were then analyzed by gas chromatography to verify that 1,1,1-trichloro-4-methyl-3-penten-2-ol was formed. Conversions and selectivities were as shown below:

| Reaction Time (hr.) | Conversion (%) | Selectivity (%) |
|---|---|---|
| 19 | 76 | 95 |
| 24 | 82 | 94 |
| 30 | 86 | 94 |
| 34 | 86 | 94 |

The product obtained after 34 hours of reaction, shown above, was subjected to reduced pressure distillation. 30 Parts of a fraction of b.p. 105°–120° C./18 mmHg were taken and recrystallized from n-hexane to isolate pure 1,1,1-trichloro-4-methyl-3-penten-2-ol.

Properties of the product were as shown below:

| m.p.; | 83° C. |
|---|---|
| IR Spectrum (KBr disk); | 1670 cm$^{-1}$ (C=C) |
|  | 3270 cm$^{-1}$ (OH) |
| NMR Spectrum (60 MHz) | $\delta^{CCl_4}_{TMS}$: |
| 1.78(s)6H; 2.63(bs)1H; 4.60 (d, J = 9Hz)1H; |  |
| 5.29(bd, J = 9Hz)1H |  |

| Elementary analysis: | C (%) | H (%) |
|---|---|---|
| Found: | 35.56 | 4.47 |
| Theoretical: | 35.41 | 4.46 |

EXAMPLE 2

5.0 Parts of 1,1,1-trichloro-4-methyl-4-penten-2-ol were heated in an oil bath at 240° C. The contents of the reaction vessel were subjected to reflux for 2 hours. The reaction products were then subjected to reduced pressure distillation to obtain 2.9 parts of a fraction of b.p. 100°–122° C./20 mmHg. The product was analyzed by gas chromatography which revealed that the product was a mixture of 1,1,1-trichloro-4-methyl-4-penten-2-ol and 1,1,1-trichloro-4-methyl-3-penten-2-ol (21:79). About 2 parts of a tarry distillation residue were formed.

EXAMPLE 3

2 Parts of 1,1,1-Trichloro-4-methyl-4-penten-2-ol were stirred at 120°–130° C. for 24 hours. The contents of the reaction vessel were subjected to gas chromatography revealing that 1,1,1-trichloro-4-methyl-4-penten-2-ol was formed with a conversion of 15% and a selectivity of 96%.

EXAMPLE 4

50 Parts of 1,1,1-tribromo-4-methyl-4-penten-2-ol [purity; above 98%] were stirred at a temperature of 130°–135° C. for 3.5 hours under an atmosphere of nitrogen. The contents of the reaction vessel were analyzed by gas chromatography revealing that 1,1,1-tribromo-4-methyl-3-penten-2-ol was formed with a conversion of 88% and a selectivity of 97%.

The contents were dissolved in diethyl ether and decolorized by treatment with active carbon. Thereafter, diethyl ether was distilled out and the resulting solid was recrystallized from petroleum ether to obtain 38 parts of 1,1,1-tribromo-4-methyl-3-penten-2-ol. Properties of the product were as shown below:

| b.p.: | 120 – 122° C./1mmHg |
|---|---|
| m.p.: | 81.5 – 82° C. |
| NMR Spectrum (60 MHz) | $\delta^{CCl_4}_{TMS}$ ; |
| 1.80(s)6H; 2.71(d, J = 6Hz)1H; 4.38 – 4.68(m)1H; | |
| 5.30 (bd, J = 8Hz)1H | |
| IR Spectrum (KBr disk); | 1670 cm$^{-1}$ (C = C) |
| | 3310 cm$^{-1}$ (OH) |

| Elementary analysis: | C (%) | H (%) |
|---|---|---|
| Found: | 21.08 | 2.49 |
| Theoretical: | 21.39 | 2.69 |

EXAMPLE 5

65 Parts of 1,1,1-tribromo-4-methyl-4-penten-2-ol were stirred at a temperature of 100°–110° C. for a predetermined time period under an atmosphere of nitrogen. The contents of the reaction vessel were analyzed by gas chromatography revealing that 1,1,1-tribromo-4-methyl-3-penten-2-ol was formed with conversions and selectivities as shown below:

| Reaction time (hr) | Conversion (%) | Selectivity to 1,1,1-tribromo-4-methyl-3-penten-2-ol (%) |
|---|---|---|
| 2.5 | 20 | 98 |
| 5 | 52 | 97 |
| 10 | 72 | 97 |
| 25 | 80 | 97 |

EXAMPLE 6

6.5 Parts of 1,1,1-tribromo-4-methyl-4-penten-2-ol were stirred at a temperature of 180°–185° C. for 5 minutes under an atmosphere of nitrogen. A small quantity of low boiling point distillation fraction was distilled out from the reaction system. The contents of the reaction vessel were analyzed by gas chromatography revealing that 1,1,1-tribromo-4-methyl-3-penten-2-ol was formed. Conversion was 89% and selectivity was 45%.

EXAMPLE 7

To 100 parts of n-hexane, 50 parts of 1,1,1-trichloro-4-methyl-4-penten-2-ol and 1.0 part of p-toluenesulfonic acid were added and the entire mass was heated under reflux for 15 hours. The contents of the reaction vessel were analyzed by gas chromatography revealing that 1,1,1-trichloro-4-methyl-3-penten-2-ol was formed. Conversion was 85% and selectivity was 96%. Upon allowing the contents to cool, crystals were formed. The crystals were 1,1,1-trichloro-4-methyl-3-penten-2-ol of the same properties as in Example 1. After filtration, yield of the product was 31 parts.

The mother liquor obtained by the filtration was a mixture of 1,1,1-trichloro-4-methyl-4-penten-2-ol and 1,1,1-trichloro-4-methyl-3-penten-2-ol (about 1:1), which was then subjected to heating under reflux to continue the isomerization until a ratio of isomers of about 2:8 was attained.

EXAMPLE 8

To 25 parts of toluene, 5 parts of 1,1,1-tribromo-4-methyl-4-penten-2-ol and 0.1 part of p-toluenesulfonic acid were added and the mass was heated under reflux for 4 hours. The reaction products were analyzed by gas chromatography revealing that 1,1,1-tribromo-4-methyl-3-penten-2-ol was formed. Conversion was 80% and selectivity was 92%. The reaction products were diluted with diethyl ether, decolorized by treatment with active carbon and subjected to reduced pressure distillation to distill out low boiling point matter. The resulting crystals were recrystallized from petroleum ether to obtain 3.2 parts of 1,1,1-tribromo-4-methyl-3-penten-2-ol having the same properties as in Example 4.

EXAMPLES 9–13

In the isomerization reaction of 1,1,1-trichloro-4-methyl-4-penten-2-ol into 1,1,1-trichloro-4-methyl-3-pentene-2-ol, differences in conversions and selectivities to 1,1,1-trichloro-4-methyl-3-penten-2-ol resulting from various reaction conditions were determined in the same manner as in Example 7. The results are shown in Table 1. Amberlyst-15 is a strongly acidic cation exchange MR-H resin [a product of Organo Co., Ltd.], and concentrations of sulfuric acid and phosphoric acid were 95% and 85%, respectively.

TABLE 1

| Example | 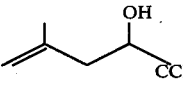 (parts) | solvent (parts) | Acid catalyst (parts) | Reaction time (° C.) | Reaction time (hr.) | Conversion (%) | Selectivity to 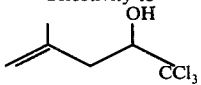 (%) |
|---|---|---|---|---|---|---|---|
| 9 | 5.0 | Benzene 25 | p-Toluenesulfonic acid 0.08 | Reflux | 15 | 85 | 95 |
| 10 | 9.0 | n-Hexane 30 | Amberlyst-15 0.05 | Reflux | 15 | 78 | 90 |
| 11 | 5.0 | Toluene 25 | Sulfuric acid 0.13 | Reflux | 7 | 80 | 72 |
| 12 | 5.0 | Toluene 25 | Phosphoric acid 0.16 | Reflux | 10 | 81 | 76 |
| 13 | 5.0 | None | p-Toluenesulfonic acid 0.005 | 115 | 6 | 87 | 80 |

EXAMPLE 14

To 100 parts of 1,1,1-trichloro-4-methyl-4-penten-2-ol [purity: above 98%], 1 part of palladium black was added and the mass was stirred at 140°–150° C. under an atmosphere of nitrogen for 18 hours. The reaction products were analyzed by gas chromatography revealing that 1,1,1-trichloro-4-methyl-3-penten-2-ol was formed. Conversion was 83% and selectivity was 94%. The reaction mixture was diluted with ether, washed with water and then subjected to filtration to separate the catalyst. Thereafter, the ether layer was dried with magnesium sulfate and subjected to reduced pressure distillation. 90 Parts of a fraction of b.p. 110°–115° C./20 mmHg were taken out and then recrystallized from n-hexane to isolate pure 1,1,1-trichloro-4-methyl-3-penten-2-ol.

EXAMPLES 15–30

To a fraction of 1,1,1-trichloro-4-methyl-4-penten-2-ol, there was added at least one substance selected from the group consisting of transition metals of Groups 6B, 7B and 8 of the Periodic Table and compounds of these transition metals, amount of the substance being 5 wt. % based on the starting 1,1,1-trichloro-4-methyl-4-penten-2-ol. The mass was stirred at 140°–150° C. for 4 hours. Thereafter, the reaction products were analyzed by gas chromatography to determine conversion and selectivity to 1,1,1-trichloro-4-methyl-3-penten-2-ol. The results are shown in Table 2.

TABLE 2

| Ex. | Catalyst | Conversion (%) | Selectivity to 1,1,1-trichloro-4-methyl-3-pentene-2-ol (%) |
|-----|----------|----------------|-----------------------------------------------------------|
| 15 | Chromium (III) acetylacetonate | 75 | 85 |
| 16 | Molybdenum disulfide | 75 | 80 |
| 17 | Tungsten trioxide | 45 | 95 |
| 18 | Manganese (III) acetylacetonate | 60 | 90 |
| 19 | Ruthenium trichloride | 75 | 60 |
| 20 | Cobalt (II) acetylacetonate | 80 | 85 |
| 21 | Hexamine-cobalt | 80 | 95 |
| 22 | Rhodium (III) acetylacetonate | 80 | 90 |
| 23 | Rhodium trichloride | 45 | 90 |
| 24 | Iridium trichloride | 70 | 95 |
| 25 | Raney-nickel | 65 | 85 |
| 26 | Nickel (II) acetylacetonate | 80 | 80 |
| 27 | Palladium chloride | 80 | 85 |
| 28 | Palladium black | 80 | 95 |
| 29 | Palladium oxide | 80 | 95 |
| 30 | Equivalent amount mixture of cobalt (II) acetyalcetonate and nickel (II) acetylacetonate | 80 | 80 |

EXAMPLE 31

To 2.0 g of 1,1,1-trichloro-4-methyl-4-penten-2-ol [purity = above 98%] were added 0.04 g of p-toluenesulfonic acid, and the mixture was stirred at 50° C. for a predetermined time period under an atmosphere of nitrogen. The reaction solution was subjected to gas chromatographic analysis revealing that 1,1,1-trichloro-4-methyl-3-penten-2-ol was formed with conversions and selectivities as shown below:

| Reaction time (hr) | Conversion (%) | Selectivity (%) |
|---|---|---|
| 16 | 51 | 98 |
| 40 | 88 | 94 |

EXAMPLE 32

To 10 g of benzene were added 2.0 g of 1,1,1-tribromo-4-methyl-4-penten-2-ol and 0.04 g of p-toluenesulfonic acid. The resulting mixture was stirred at 50° C. for 20 hours under an atmosphere of nitrogen. The reaction solution was analyzed by using liquid chromatograph [Waters, ALC/GPC-244 Type, $\mu$-Bondapak $C_{18}$ 4 mm$\phi\times$ 30 cm, Water/Methanol = 30/70 (Vol. %), 20° C. Differential Refractometer] revealing that 1,1,1-tribromo-4-methyl-3-penten-2-ol was formed in a yield of about 70% based on the starting 1,1,1-tribromo-4-methyl-4-penten-2-ol.

The 1,1,1,-trihalogeno-4-methyl-4-penten-2-ol used in the above examples was prepared by one of processes shown in the following Reference Examples 1–9.

REFERENCE EXAMPLE 1

A mixture of 59.0 psrts of chloral [trichloroacetaldehyde], 29.2 parts of isobutene and 80 parts of petroleum ether was cooled to a temperature in the range of from $-20°$ C. to $-5°$ C. 4.2 Parts of anhydrous tin tetrachloride were added thereto dropwise and the mass was stirred for 5 hours while the temperature was kept at that point. Thereafter, the reaction mixture was diluted with diethyl ether and washed with about 50 parts of water. Low boiling point matter was distilled out from the organic layer. After reduced pressure distillation, 69.2 parts (yield: 85%) of 1,1,1-trichloro-4-methyl-4-penten-2-ol of b.p. 104°–107° C./22 mmHg were obtained. Properties of the product were as shown below:

NMR Spectrum (60 MHz) $\delta_{TMS}^{CCl_4}$;
1.80(bs)3H; 2.0–3.0(m)3H; 3.9–4.2(m)1H; 4.88(bs)2H

REFERENCE EXAMPLE 2

A mixture of 28.1 parts of tribromoacetaldehyde [bromal], 16.8 parts of isobutene and 15 parts of petroleum ether was cooled to a temperature in the range of from $-10°$ to $-5°$ C. 1.3 Parts of anhydrous aluminum chloride were added thereto portionwise and the mass was stirred for 5 hours while the temperature was kept at that point.

As the reaction proceeded, crystals were precipitated in the reaction vessel. At the final period of the reaction, diethyl ether was added thereto to obtain the homogeneous solution. The solution was then stirred at room temperature for 30 minutes and then 20 parts of water were added to the solution. The organic layer was decanted, from which low boiling point matter was distilled out. After reduced pressure distillation, 28.7 parts (yield: 85%) of 1,1,1-tribromo-4-methyl-4-penten-2-ol of b.p. 108°–110° C./0.3 mmHg and m.p. 64°–65° C. were obtained.

Properties of the product were as shown below:

| IR Spectrum (KBr disk) | 1645 cm$^{-1}$ (C=O C), 3500 cm$^{-1}$ (OH) | |
|---|---|---|
| NMR Spectrum (60 MHz) | $\delta_{TMS}^{CCl_4}$; | |
| 1.82(s)3H; 2.03 – 3.05(m)2H; 3.87 – 4.10(m)1H; 4.88(s)2H | | |
| Elementary analysis: | C (%) | H (%) |
| Found: | 21.09 | 2.55 |
| Theoretical: | 211.39 | 2.69 |

REFERENCE EXAMPLES 3–9

Tribromoacetaldehyde was reacted with isobutene in the presence of various acid catalysts. The reaction conditions and yield of 1,1,1-tribromo-4-methyl-4-penten-2-ol are shown in following Table 3.

pared by the process described above, were added to the solution. The mixture was agitated for 2 hours under

TABLE 3

| Reference Example | Tribromo-acetaldehyde (parts) | Isobutene (parts) | Acid Catalysts (parts) | Solvent (parts) | Reaction temp. (° C.) | Reaction time (hr.) | Yield of 1,1,1-tribromo-4-methyl-4-pentene-2-ol (%) |
|---|---|---|---|---|---|---|---|
| 3 | 28.1 | 16.8 | $AlCl_3$ 1.3 | Petroleum ether 15 | $-10 \sim +5$ | 3 | 85 |
| 4 | 28.1 | 16.8 | $AlBr_3$ 2.7 | Petroleum ether 15 | $-10 \sim +5$ | 3 | 80 |
| 5 | 28.1 | 16.8 | $SnCl_4$ 2.6 | Petroleum ether 15 | $-10 \sim +5$ | 3 | 73 |
| 6 | 9.4 | 5.6 | $ZnCl_2$ 0.45 | Petroleum ether 15 | $-10 \sim +10$ | 2 | 52 |
| 7 | 9.4 | 5.6 | $BF_3 \cdot O(C_2H_5)_2$ 0.37 | Petroleum ether 15 | $-10 \sim +10$ | 2 | 62 |
| 8 | 9.4 | 5.6 | $H_2SO_4$ 0.33 | Petroleum ether 15 | $-10 \sim +25$ | 3 | 42 |
| 9 | 9.4 | 5.6 | $H_3PO_4$ 0.33 | — | $-10 \sim +25$ | 3 | 35 |

As explained in the Reference Examples 10 to 12 described below, 1,1,1-trihalogeno-4-methyl-3-penten-2-ol obtained by the process of the present invention may be used as the starting material in the synthesis of 3,3-dimethyl-4,6,6-trihalogeno-5-hexenoic esters, thereafter the 3,3-dimethyl-4,6,6-hexenoic esters may be converted to 2,2-dimethyl-3-(2',2'-dihalogenovinyl)cyclopropanecarboxylic esters by treating with a basic reagent.

REFERENCE EXAMPLE 10

To the mixture consisting of 61.2 parts of 1,1,1-trichloro-4-methyl-4-penten-2-ol obtained by the process similar to that described in the Reference Example 1, and 120 parts of toluene, 1.2 parts of p-toluenesulfonic acid were added, and the resultant mixture was heated for 1.5 hours under reflux of toluene with stirring.

The contents of the reaction vessel were analyzed by gas chromatography revealing that 1,1,1-trichloro-4-methyl-3-penten-2-ol was formed. Conversion was 85% and selectivity was 95%. Thereafter, 97.3 parts of ethyl orthoacetate were added to the reaction mixture, and said mixture was heated at 110° to 120° C. for 2 hours and for another 4 hours at 120° to 155° C. with stirring. The ethanol formed as the by-product during the reaction was continuously distilled with toluene from the reaction system. After completion of the reaction, the liquid reaction mixture was directly subjected to distillation under reduced pressure to obtain 52.5 parts of an oily fraction having a boiling point of 83° to 84° C. under 28 mmHg, i.e., ethyl 3,3-dimethyl-4,6,6-trichloro-5-hexenoate. The yield was 64% based on the starting 1,1,1-trichloro-4-methyl-4-penten-2-ol.

Properties of the thus obtained product were as follows:

NMR Spectrum (100 MHz) $\delta_{TMS}^{CCl_4}$:
1.08(s)6H; 1.20(t, J = 7Hz)3H; 2.14(d, J = 14Hz)1H; 2.42(d, J = 14Hz)1H; 4.01(q, J = 7Hz)2H; 4.83(d, J = 11Hz)1H; 5.95(d, J = 11Hz)1H Elementary Analysis Values: Found: C = 43.77%, H = 5.47%. Calculated: C = 43.90%, H = 5.53%.

IR Spectrum (neat): 1610 cm$^{-1}$ (C=C), 1730 cm$^{-1}$ (C=O)

Thereafter, 2.8 parts of metallic sodium were dissolved in 150 parts of anhydrous ethanol, and 27.4 parts of ethyl 3,3-dimethyl-4,6,6-trichloro-5-hexenoate prereflux of ethanol. The reaction mixture was cooled by ice water and neutralized with hydrogen chloride-saturated ethanol solution. The precipitated solids were removed by filtration, and ethanol was distilled from the filtrate. The filtrate was diluted with diethyl ether, washed with water and then dried on anhydrous magnesium sulfate. The solvent was removed by distillation, and the residue was subjected to distillation under reduced pressure to obtain 21.0 parts of ethyl 2,2-dimethyl-3-(2',2'-dichlorovinyl)cyclopropane carboxylate having a boiling point of 72° to 73° C. under 0.3 mmHg. The yield was 89%. The cis:trans ratio of the product determined by gas chromatography was 25:75.

NMR Spectrum (60 MHz) $\delta_{TMS}^{CDCl_3}$; CDCl$_3$ TMS;
1.20(s), 1.27(t, J = 7Hz), 1.30(s)9H; 1.55–2.40(m) 2H; 4.16(q, J = 7Hz), 4.18(q, J = 7Hz)2H; 5.68(d, J = 8Hz), 6.34(d, J = 8Hz)1H Elementary Analysis Values: Found: C = 50.51%, H = 6.24% Calculated: C = 50.65%, H = 5.95%

IR Spectrum (neat) 1620 cm$^{-1}$ (C=C), 1730 cm$^{-1}$ (C=O)

REFERENCE EXAMPLE 11

0.1 Part of isobutylic acid was added to the mixture of 10.2 parts of pure 1,1,1-trichloro-4-methyl-3-penten-2-ol obtained by the process described in Example 14, and 16.2 parts of ethyl orthoacetate, and the mixture was agitated at 130° to 145° C. for 2 hours in an atmosphere of nitrogen, and for another 2 hours at 145° to 155° C. The ethanol formed during the reaction was continuously distilled from the reaction system. The reaction mixture was subjected to the same process as mentioned in the Reference Example 10 to obtain 11.1 parts of ethyl 3,3-dimethyl-4,6,6-trichloro-5-hexenoate. The yield was 81%.

2.7 Parts of ethyl 3,3-dimethyl-4,6,6-trichloro-5-hexenoate, thus obtained were dissolved in 25 parts of dry benzene, and 1.9 parts of sodium t-butylate were added to the solution and the mixture was agitated at room temperature for 1 hour. The liquid reaction mixture was poured in ice water and extracted with diethyl ether. Ether and benzene were removed from the organic layer by distillation under reduced pressure to obtain 2.1 parts of ethyl 2,2-dimethyl-3-(2',2'-dichlorovinyl)-cyclopropanecarboxylate. The yield was 89%.

REFERENCE EXAMPLE 12

0.3 Parts of isobutylic acid was added to the mixture of 33.7 parts of pure 1,1,1-tribromo-4-methyl-3-penten-2-ol obtained by the process described in Example 4, and 48.7 parts of ethyl orthoacetate, and the mixture was agitated at 130° to 145° C. for 2 hours in an atmosphere of nitrogen, and for another 2 hours at 145° to 155° C. The ethanol formed during the reaction was continuously distilled from the reaction system. The reaction was directly subjected to distillation under reduced pressure to obtain 28.3 parts of ethyl 3,3-dimethyl-4,6,6-tribromo-5-hexenoate as an oily fraction having a boiling point of 125° to 127° C. under 0.25 mmHg. The yield was 70% based on the starting 1,1,1-tribromo-4-methyl-3-penten-2-ol.

Properties of the thus obtained product were as follows:

IR Spectrum (neat) 1600 cm$^{-1}$(C=C), 1730 cm$^{-1}$(C=O)

NMR Spectrum (60 MHz) $\delta_{TMS}^{CCl_4}$:
1.12(s)6H; 1.22(t, J = 7Hz)3H; 2.17(d, J = 15Hz)1H; 2.49(d, J = 15Hz)1H; 4.08(q, J = 7Hz)2H; 4.93(d, J = 11Hz)1H; 6.66(d, J = 11Hz)1H 4.1 Parts of ethyl 3,3-dimethyl-4,6,6-dibromo-5-hexenoate, thus obtained were dissolved in 35 parts of dry benzene, and 1.9 parts of sodium t-butylate were added to the solution and the mixture was subjected to the same process as mentioned in the Reference Example 11 to obtain 3.2 parts of ethyl 2,2-dimethyl-3-(2',2'-dibromovinyl)cyclopropane carboxylate as an oily fraction having a boiling point of 92° to 94° C. under 0.5 mmHg. The yield was 98%.

REFERENCE EXAMPLE 13

Isomerization of 1,1,1-trichloro-4-methyl-4-penten-2-ol by using aluminum chloride at room temperature To a solution of 15.0 g of 1,1,1-trichloro-4-methyl-4-penten-2-ol in 50 ml of n-hexane was added 1.0 g of aluminum chloride, and the mixture was stirred at room temperature (25° C.) for 8 hours. The reaction solution was subjected to gas chromatographic analysis revealing that 1,1,1-trichloro-4-methyl-3-penten-2-ol was not formed.

REFERENCE EXAMPLE 14

Thermal isomerization of 3-methyl-3-buten-1-ol 10 g of 3-methyl-3-buten-1-ol were stirred under reflux (at 135° C.) for 15 hours. The reaction solution barely showed a light yellow color. The reaction solution was subjected to gas chromatographic analysis revealing a trace amount of 3-methyl-2-buten-1-ol.

REFERENCE EXAMPLE 15

Thermal isomerization of 3-methyl-3-buten-1-ol in the presence of p-toluenesulfonic acid To 5 g of 3-methyl-3-buten-1-ol was added 0.12 g of p-toluene-sulfonic acid, and the mixture was stirred under reflux (at 135° C.) for 3 hours. The reaction solution showed a brown color. The reaction solution was subjected to gas chromatographic analysis revealing that 3-methyl-2-buten-1-ol was formed in a yield of about 4% based on the starting 3-methyl-3-buten-1-ol. In addition, a large amount of unknown products was formed.

Thermal stability of 3-methyl-2-buten-1-ol in the presence of p-toluenesulfonic acid To 30 g of 3-methyl-2-buten-1-ol [prenol] was added 0.74g of p-toluenesulfonic acid, and the mixture was stirred under reflux (at 130°–140° C.) for 3 hours. The reaction solution separated into two layers. The lower layer comprised water and the upper layer was subjected to gas chromatographic analysis revealing that about 4% of the starting prenol remained and that diprenyl ether was formed in a yield of about 50% based on the starting prenol together with unknown products. After distillation under reduced pressure was isolated diprenyl ether having the following properties.

bp: 100°–103° C./22 mmHg
NMR Spectrum (60MHz) $\delta_{TMS}^{CCl_4}$:
1.67, 1.74 (each s)12H; 3.97(d, J = 7Hz)4H; 5.19–5.60(m)2H While the invention has now been described in terms of certain preferred embodiments, and exemplified with respect thereto, the skilled artisan will appreciate that various modifications, changes, substitutions, and omissions may be made without departing from the spirit thereof. Accordingly, it is intended that the scope of the present invention be limited solely by that of the following claims.

What is claimed is:

1. A process for preparing a 1,1,1-trihalogeno-4-methyl-3-penten-2ol of the formula:

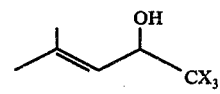

wherein each X represents Cl or Br, which comprises noncatalytically thermally isomerizing a 1,1,1-trihalogeno-4-methyl-4-penten-2-ol of the formula:

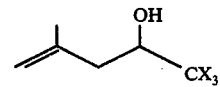

wherein each X is as defined above, at a temperature ranging from 100° C. to 240° C.

2. The process as defined by claim 1, wherein the temperature of thermal isomerization is from 140° C. to 240° C.

3. The process as defined by claim 1, conducted under a blanket of inert gas.

4. The process as defined by claim 1, conducted in inert solvent solution.

* * * * *

UNITED STATES PATENT OFFICE
CERTIFICATE OF CORRECTION

Patent No. 4,117,247　　　　　　　　　Dated September 26, 1978

Inventor(s) Fumio MORI; Yoshiaki OMURA; Takashi NISHIDA and Kazuo ITOI

It is certified that error appears in the above-identified patent and that said Letters Patent are hereby corrected as shown below:

Under "Foreign Application Priority Data", the application numbers "49-2064" and "49-2065" should be -- 50-2064 -- and 50-2065 --, respectively;

Column 4, line 60, "1,1,1-trihalogeno-4-methyl-3-penten-2-ols" should be -- 1,1,1-trihalogeno-4-methyl-3-penten-2-ol --;

Column 5, line 14, "1,1,1-halogeno-4-methyl-3-penten-2-ol" should be -- 1,1,1-trihalogeno-4-methyl-3-penten-2-ol --;

Column 6, line 57, "1,1,1-Trichloro-4-methyl-4-penten-2-ol" should be -- 1,1,1-trichloro-4-methyl-4-penten-2-ol --;

Column 10, line 20, "59.0 psrts" should be -- 59.0 parts --;

Column 10, line 63, "Theoretical　211.39　2.69" should be -- Theoretical 21.39　2.69 --;

Column 12, line 37, cancel "$CDCl_3$ TMS;";

Column 13, lines 25 and 26, "ethyl 3,3-dimethyl-4,6,6-dibromo-5-hexenoate" should be -- ethyl 3,3-dimethyl-4,6,6-tribromo-5-hexenoate --.

Signed and Sealed this

Twenty-second Day of May 1979

[SEAL]

Attest:

RUTH C. MASON
*Attesting Officer*

DONALD W. BANNER
*Commissioner of Patents and Trademarks*